United States Patent
Poland (10) Patent No.: US 6,709,395 B2
(45) Date of Patent: Mar. 23, 2004

(54) SYSTEM AND METHOD FOR ELECTRONICALLY ALTERING ULTRASOUND SCAN LINE ORIGIN FOR A THREE-DIMENSIONAL ULTRASOUND SYSTEM

(75) Inventor: McKee Poland, Andover, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/179,349
(22) Filed: Jun. 25, 2002

(65) Prior Publication Data
US 2003/0236461 A1 Dec. 25, 2003

(51) Int. Cl.[7] .................................. A61B 8/02
(52) U.S. Cl. ................. 600/447; 600/437; 600/443; 73/606; 73/625
(58) Field of Search ............... 600/437–472; 73/602–625

(56) References Cited

U.S. PATENT DOCUMENTS

| | | | | |
|---|---|---|---|---|
| 4,368,643 A | * | 1/1983 | Tachita et al. ............ 73/626 |
| 4,694,434 A | * | 9/1987 | von Ramm et al. ........ 367/7 |
| 5,148,810 A | * | 9/1992 | Maslak et al. ............ 600/447 |
| 5,235,986 A | * | 8/1993 | Maslak et al. ............ 600/447 |
| 5,261,408 A | * | 11/1993 | Maslak et al. ............ 600/447 |
| 5,546,807 A | * | 8/1996 | Oxaal et al. ............ 73/606 |
| 5,549,111 A | * | 8/1996 | Wright et al. ............ 600/447 |
| 6,102,860 A | * | 8/2000 | Mooney ................ 600/443 |
| 6,238,346 B1 | * | 5/2001 | Mason ................ 600/459 |
| 6,276,211 B1 | * | 8/2001 | Smith ................ 73/626 |
| 6,443,896 B1 | * | 9/2002 | Detmer ................ 600/445 |

FOREIGN PATENT DOCUMENTS

| | | |
|---|---|---|
| EP | 0442450 A2 | 8/1991 |
| WO | 9603918 A1 | 6/1996 |

OTHER PUBLICATIONS

"Three–Dimensional Ultrasound Imaging", T. R. Nelson et al, Ultrasound in Med. & Biol., vol. 24, No. 9, pp. 1243–1270, 1998.

\* cited by examiner

*Primary Examiner*—Dennis Ruhl
*Assistant Examiner*—William C. Jung
(74) *Attorney, Agent, or Firm*—John Vodopia (57) ABSTRACT

A system and method for individually varying the orientation of scan lines in at least two dimensions in an ultrasound scan are disclosed. In one embodiment, the invention includes a system for generating a three-dimensional ultrasound volume scan, comprising a transducer probe having elements arranged in a plurality of dimensions and a system controller capable of generating a scan line apparently emanating from a location other than the geographic center of the transducer probe.

27 Claims, 5 Drawing Sheets

STEERING ANGLE (THETA)   ELEVATION ANGLE (ZETA)

SYSTEM AND METHOD FOR ELECTRONICALLY ALTERING ULTRASOUND SCAN LINE ORIGIN FOR A THREE-DIMENSIONAL ULTRASOUND SYSTEM

TECHNICAL FIELD

The present invention relates generally to ultrasonic diagnostic systems, and, more particularly, to an ultrasonic diagnostic system that is capable of electronically adjusting the apparent origin of ultrasound scan lines from a transducer.

BACKGROUND OF THE INVENTION

Ultrasonic transducers and imaging systems have been available for quite some time and are particularly useful for non-invasive medical diagnostic imaging. Ultrasonic transducers are typically formed of either piezoelectric elements or of micro-machined ultrasonic transducer (MUT) elements. When used in transmit mode, the transducer elements are excited by an electrical pulse and in response, emit ultrasonic energy. When used in receive mode, acoustic energy impinging on the transducer elements is converted to a receive signal and delivered to processing circuitry associated with the transducer.

The transducer is typically connected to an ultrasound imaging system that includes processing electronics, one or more input devices and a suitable display on which the ultrasound image is viewed. The processing electronics typically include a transmit beamformer that is responsible for developing an appropriate transmit pulse for each transducer element, and a receive beamformer that is responsible for processing the receive signal received from each transducer element.

An ultrasonic transducer is typically combined with associated electronics in a housing. The assembly is typically referred to as an ultrasonic probe. Typically, ultrasonic probes are classified as either one-dimensional (1D) probes having a single element wide array of elements, or two-dimensional (2D) probes having a multiple element wide array. Furthermore, a probe referred to as a "bi-plane" probe includes two orthogonally positioned 1D arrays that may or may not intersect. A relatively new 2D probe, referred to as a "matrix probe" includes transducer elements arranged in two dimensions where each element is individually controllable, resulting in an ultrasound probe the scan lines of which can be electronically steered in two dimensions. Each dimension of a matrix probe can be thought of as a stack of contiguous linear arrays.

A matrix probe can comprise either a "fully sampled" or a "sparsely sampled" aperture. In a fully sampled aperture, every transducer element is individually addressable and controllable, and all elements are contiguous. In a sparsely sampled aperture, a subset of the physical set of transducer elements is addressed and controlled, or equivalently, there is a pattern of physical gaps between some elements such that they are not all contiguous. Sparsely sampled 2D arrays allow for fewer system connections (fewer channels) while still achieving distribution of the acoustic elements in two dimensions. However, a significant drawback of sparse 2D arrays is the loss of ability to control scan beam shape.

Figure 1:
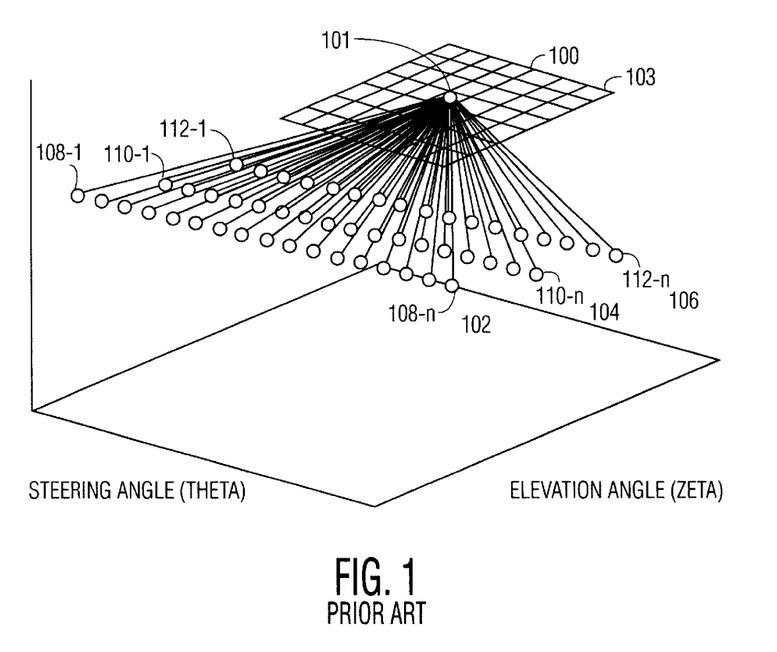
FIG. 1 is a schematic diagram illustrating the manner in which an existing ultrasound probe interrogates a volume.

A 2D-matrix probe can be used to develop three-dimensional (3D) ultrasound images. FIG. 1 is a schematic diagram illustrating the manner in which an existing ultrasound probe interrogates a volume. Ultrasound data is typically acquired in frames, where each frame represents one or more sweeps of an ultrasound beam emanating from the face of the probe 100. The probe 100 includes a two-dimensional array of transducer elements; an exemplar one of which is illustrated using reference numeral 103. Such a sweep is typically developed by generating a large number of individual scan lines along one scan plane. An example of one scan plane, or "slice," is illustrated using reference numeral 102 and the scan plane comprises individual scan lines 108-1 through 108-n. In this case, each slice is in the shape of a sector, and the "origin" 101 of each scan line is located at the center of the surface of the physical face of the probe 100.

The scan lines are typically steered in 2 dimensions during scan sweeps to create a set of rastered scan slices, exemplar ones of which are illustrated as slices 102, 104 and 106, where each slice interrogates a 2-dimensional "sector region" of the field of view. In effect, each slice 102, 104 and 106 represents a traditional two-dimensional sweep, with each sweep being displaced in elevation from the neighboring sweep. Those having ordinary skill in the art will recognize that trapezoidal or parallelogram shapes can be generated for each of the slices instead of sectors. Furthermore, a large number of such slices, slightly displaced in elevation, can be used to interrogate a volume.

Assembling the data from the sector slices produces a three-dimensional set of data referred to as a scan volume. Since all of the lines originate from the same point, the rendered 3D volume appears as a pyramid or cone, where the apex of the volume is the scan origin at the transducer probe face, which is located at the patient's skin surface.

When conventional ultrasound imaging systems develop this volume scan, they typically generate multiple slices in at least two dimensions. These multiple slices generate ultrasound data for the volume occupied by the slices. To produce three-dimensional images, this volume of data is then processed by the ultrasound imaging system to create an image for display on a two-dimensional surface (such as the surface of the CRT type display) that has the appearance of being three-dimensional. Such processing is typically referred to as a rendering.

Figure 2:
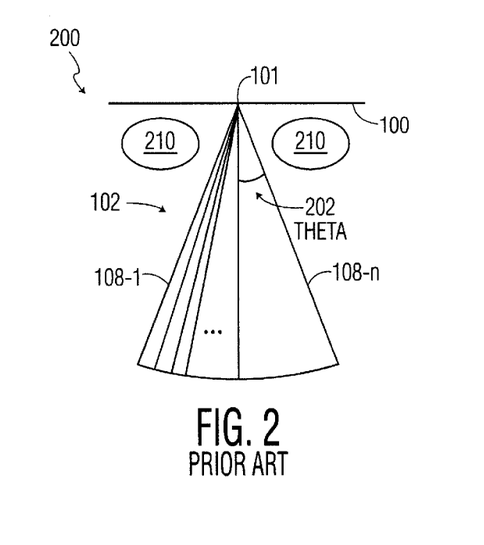
FIG. 2 is a graphical representation of one of the ultrasound slices of FIG. 1.

Unfortunately, the existing "pyramid" or "cone-shaped" sector scan format limits the field of view near the skin surface. This situation is illustrated in FIG. 2, which is a graphical representation of one of the ultrasound slices of FIG. 1. The slice 102 includes scan lines 108-1 through 108-n emanating from the origin 101 of the transducer probe 100. Typically, the transducer probe rests against the patient's skin, thereby providing a limited field of view near the transducer probe. This "near field" is illustrated in FIG. 2 as the areas denoted 210. These near field areas 210 are beyond the maximum steering angle (theta ($\theta$)) 202 achievable using the scan lines 108-1 through 108-n. This can be a problem in cardiac scanning when the probe is near the apex of the heart, such as with an apical 4 chamber view. In such a view, it is often desirable to scan and display a wider field of view near the apex (origin 101) than is allowed by the scan format. A wide field of view near the probe face is also desired for certain abdominal and peripheral vascular imaging but, is not available when the sector slice format is used to generate the 3D image.

Further, the "line density"—defined as the number of scan lines per angle step in a slice—is adversely constrained by the scan format. To achieve sufficient spatial sampling in the far field (away from the probe face), the line density is increased: more lines per angle step. This results in wasteful oversampling in the near field, where the lines crowd together near the origin.

Another drawback of conventional ultrasound scanning systems is when using contrast agents in ultrasound scanning. Several problems are posed by the restriction to scanning a set of sector slices. The problems share a common root cause, which is the uneven distribution of acoustic power in the scanned volume. For example, in the near field, because scan lines are denser, there is disproportionate destruction of contrast agent microbubbles compared to destruction in the far field. Contrast agent applications, which evaluate body functions by measuring the concentration of contrast agent in tissue, can produce distorted results due to the uneven pattern of microbubble destruction.

Further, the generation and measurement of harmonic resonance in tissue echoes, a technique now widely used to improve image quality, is undesirably constrained by the sector scan format. Harmonic resonance generation is dependent on many factors in the ultrasound scanner, including transmit frequency, output pulse power, as well as factors in the medium itself. Many of these factors are already constrained by hardware limitations, FDA power limits, and the variability of human tissue. Manipulation of the scan line spacing and direction can compensate for some of these factors. However, the sector format generally prevents such manipulation.

Therefore, it would be desirable to have an ultrasound imaging system capable of displaying three-dimensional data in both near field and far field, while overcoming the above mentioned shortcomings of the conventional sector scan format.

SUMMARY

Embodiments of the invention include a system and method for individually varying the orientation of scan lines in at least two dimensions. In one embodiment, the invention includes a system for generating a three-dimensional ultrasound volume scan, comprising a two-dimensional transducer probe having elements arranged in a plurality of dimensions, and a system controller capable of generating a scan line apparently emanating from a location other than the geographic center of the transducer probe.

Other systems, methods, computer readable media, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE PREFERRED EMBODIMENT

The invention described hereafter is applicable to any ultrasound imaging system that uses a probe having a two-dimensional array of individually controllable elements that can be used to interrogate a three-dimensional volume. The following description is presented in terms of routines and symbolic representations of data bits within a memory, associated processors, and possible networks or networked devices. These descriptions and representations are used by those having ordinary skill in the art to effectively convey the substance of their work to others having ordinary skill in the art. A routine embodied in software is here, and generally, intended to be a self-consistent sequence of steps or actions leading to a desired result. Thus, the term "routine" is generally used to refer to a series of operations stored in a memory and executed by a processor. The processor can be a central processor of an ultrasound imaging system or can be a secondary processor of the ultrasound imaging system. The term "routine" also encompasses such terms as "program," "objects," "functions," "subroutines," and "procedures."

In general, the sequence of steps in the routines requires physical manipulation of physical quantities. Usually, though not necessarily, these quantities take the form of electrical or magnetic signals capable of being stored, transferred, combined, compared or otherwise manipulated. Those having ordinary skill in the art refer to these signals as "bits," "values," "elements," "characters," "images," "terms," "numbers," or the like. It should be understood that these and similar terms are to be associated with the appropriate physical quantities and are merely convenient labels applied to these quantities.

In the present application, the routines, software, and operations are machine operations performed in conjunction with human operators. In general, the invention relates to method steps, software and associated hardware including a computer readable medium configured to store and execute electrical or other physical signals to generate other desired physical signals.

The apparatus of the invention is preferably constructed for the purpose of ultrasonic imaging. However, a general-purpose computer can perform the methods of the invention or other networked device selectively activated or reconfigured by a routine stored in the computer and coupled to ultrasound imaging equipment. The procedures presented herein are not inherently related to any particular ultrasonic imaging system, computer or apparatus. In particular, various machines may be used with routines in accordance with the teachings of the invention, or it may prove more convenient to construct more specialized apparatus to perform the method steps. In certain circumstances, when it is desirable that a piece of hardware possess certain characteristics, these characteristics are described more fully below.

With respect to the software routines described below, those having ordinary skill in the art will recognize that there are a variety of platforms and languages for creating instruction sets for performing the routines described below. Those having ordinary skill in the art will also recognize that the choice of the exact platform and language is often dictated by the specifics of the actual system constructed, such that what may work for one type of system may not be efficient on another system.

Figure 3:
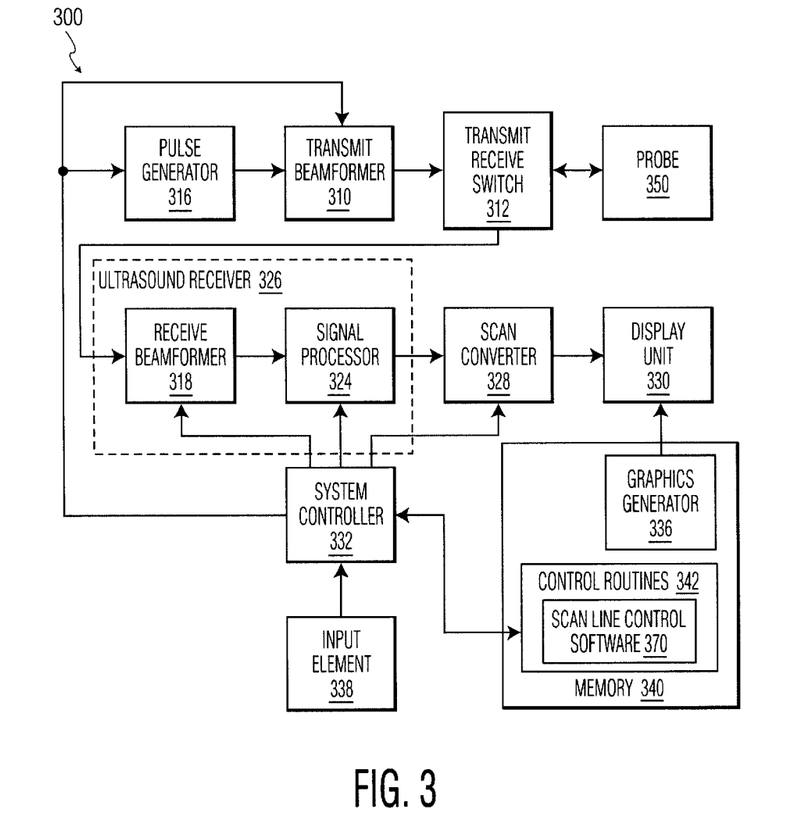
FIG. 3 is a block diagram illustrating an ultrasound imaging system in accordance with an embodiment of the invention.

FIG. 3 is a block diagram illustrating an ultrasound imaging system 300 in accordance with an embodiment of the invention. It will be understood by those having ordinary skill in the art that the ultrasound imaging system 300, as illustrated in FIG. 3, and the operation thereof as described below, is intended to be generally representative of such systems and that any particular system may differ significantly from that shown in FIG. 3. The ultrasound imaging system 300 includes a transmit beamformer 310 coupled through a transmit receive (T/R) switch 312 to a probe 350. While the probe 350 may be any transducer probe, a matrix transducer probe will be discussed for simplicity. The matrix probe 350 includes a matrix transducer array having a plurality of transducer elements arranged across two dimensions. The system 300 can randomly select any point on the matrix probe 350 as the point from which the ultrasonic energy is projected. While the matrix probe 350 will be referred to as a fully sampled array, a sparse array configuration is also possible. As described above, a fully sampled array is one in which each element is individually addressable. Either fully sampled or sparse array configurations may benefit from the various embodiments of the invention to be described below.

The T/R switch 312 typically includes one switch element for each transducer element. Alternatively, the matrix probe 350 may have multiplexing circuitry, or the like, to reduce the number of leads between the T/R switch 312 and the matrix probe 350, thereby reducing the number of required switches. The transmit beamformer 310 receives pulsed sequences from a pulse generator 316. The matrix probe 350, energized by the transmit beamformer 310, transmits ultrasound energy into a region of interest in a patient's body and receives reflected ultrasound energy, commonly referred to as echoes, from various structures and organs within the body. As is known by those having ordinary skill in the art, by appropriately delaying the waveforms applied to each transducer element by the transmit beamformer 310, a focused ultrasound beam may be transmitted from the matrix probe 350.

The matrix probe 350 is also coupled, through the T/R switch 312, to a receive beamformer 318. Ultrasound energy from a given point within the patient's body is received by the transducer elements at different times. The transducer elements convert the received ultrasound energy to transducer signals which may be amplified, individually delayed and then summed by the receive beamformer 318 to provide a beamformed signal that represents the received ultrasound levels along a desired receive line ("beam"). The receive beamformer 318 may be a digital beamformer including an analog-to-digital converter for converting the transducer signals to digital values, or may be an analog beamformer. As known to those having ordinary skill in the art, the delays applied to the transducer signals may be varied during reception of ultrasound energy to effect dynamic focusing. The process is repeated for multiple scan lines to create a frame of data for generating an image of the region of interest in the patient's body.

Even though known systems employing matrix probes concentrate on scanning complete volumes, the matrix probe 350 is capable of providing a variety of scan patterns such as a sector scan, where scan lines may appear to originate at any point on the matrix probe 350 and are directed at different angles, a linear scan, a curvilinear scan and other scan patterns.

The receive beamformed signals are then applied to a signal processor 324, which processes the beamformed signal for improved image quality. The receive beamformer 318 and the signal processor 324 comprise an ultrasound receiver 326. The output of the signal processor 324 is supplied to a scan converter 328, which converts sector scan and other scan pattern signals to conventional raster scan display formats. The output of the scan converter 328 is supplied to a display unit 330, which displays an image of the region of interest in the patient's body.

The system controller 332 provides overall control of the system. The system controller 332 performs timing and control functions and typically includes a microprocessor operating under the control of graphics generator 336 and control routines 342, both contained within memory 340. The control routines 342 also include scan line control software 370. As will be described in further detail below, the control routines 342, scan line control software 370, and the graphics generator 336, in cooperation with the system controller 332 enable the ultrasound imaging system 300 to project scan lines that can be independently controlled in multiple dimensions, have a point of origin other than the surface of the transducer, and can be steered at any angle.

For example, scan lines that comprise one or more scan slices can be individually adjusted in two dimensions (i.e., steering angle (typically referred to as theta) and elevation angle (typically referred to as zeta), essentially allowing the apex (or point of origin) of a sector scan slice to appear at a location other than the physical center of the transducer. In this manner, scan lines may be controlled so that they appear to emanate from different points on the transducer face. In such fashion, it is possible for the ultrasound imaging system 300 to interrogate a three-dimensional volume and provide a flexible field of view that allows superior near field and far field imaging.

The system controller 332 also uses the memory 340 to store intermediate values, including system variables describing the operation of the ultrasound imaging system 300. Although not shown, an external storage device may be used for permanent and/or transportable storage of data. Examples of devices suitable for use as an external storage element include a floppy disk drive, a CD-ROM drive, a videotape unit, etc.

In accordance with an aspect of one embodiment of the invention, a scan pattern corresponding to and designed to provide a desired ultrasound image can be generated by the system controller 332 upon input from the scan line control software 370. The scan pattern is then implemented by the transmit beamformer 310 and the receive beamformer 318 so that the matrix probe 350 transmits and receives the selected scan lines.

A user communicates commands to the ultrasound imaging system 300 via the input element 338, which may include, among other devices, a mouse, keyboard, stylus, or may include a combination of input devices, such as keys, sliders, switches, touch screens, a track ball, or other input devices that enable the user of the ultrasound imaging system 300 to communicate the desired ultrasound image to the system controller 332. When the desired ultrasound image is communicated to the system controller 332, the system controller 332, in cooperation with the control routines 342, the scan line control software 370, and the graphics generator 336, determines the appropriate scan lines that should be projected by the matrix probe 350 to achieve the desired ultrasound image communicated to the system controller 332 via input element 338. The system controller 332 then communicates with the pulse generator 316 and the transmit beamformer 310 in order to generate such appropriate scan lines.

In an alternative system configuration, different transducer elements are used for transmitting and receiving. In such a configuration, the T/R switch 312 may not be required, and the transmit beamformer 310 and the receive beamformer 318 may be connected directly to the respective transmit and receive transducer elements.

Figure 4:
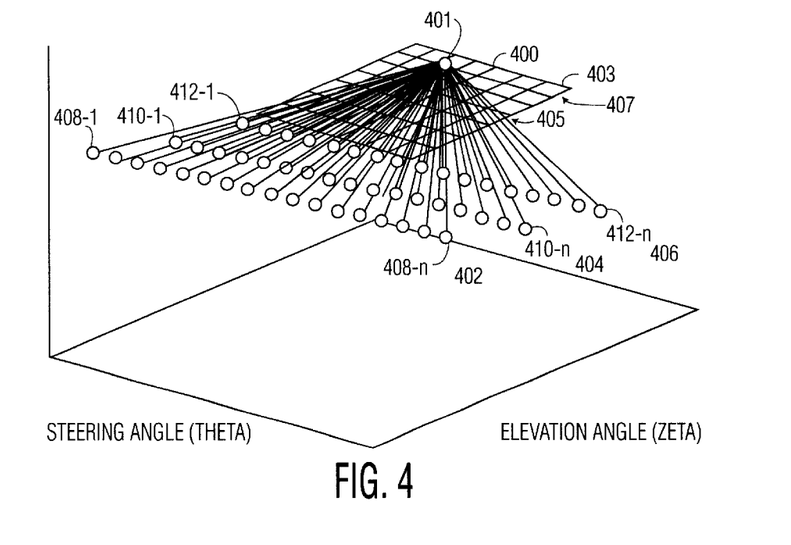
FIG. 4 is a graphical illustration showing a series of scan slices and constituent scan lines obtained using the ultrasound imaging system of FIG. 3.

FIG. 4 is a graphical illustration showing a series of scan slices and constituent scan lines generated using the ultrasound imaging system 300 of FIG. 3. The scan slices 402, 404 and 406 each include a plurality of individual scan lines 408-1 through 408-n, 410-1 through 410-n, and 412-1 through 412-n, respectively. Although only three scan slices 402, 404 and 406 are illustrated in FIG. 4 for simplicity, many additional scan slices would typically be generated during an ultrasound scan operation. The scan lines shown in FIG. 4 are generated by the matrix transducer probe 400, which includes a plurality of individual transducer elements, an exemplar one of which is illustrated using reference numeral 403.

In accordance with this embodiment of the invention, the origin 401 of all the scan lines in scan slices 402, 404 and 406 is located behind the face 407 the transducer probe 400. By moving the apparent origin of the scan lines away from the surface of the transducer probe 400, each scan line appears to have a virtual point of emanation (VPE) that appears in a different location on the face 407 of the transducer probe 400. For example, the VPE 405 of the scan line 412-n appears at a location on the surface of the face 407 other than the geographic center of the transducer probe 400. Further, in the case where each transducer element 403 transmits as well as receives ultrasound energy, each scan line also has a virtual point of reception (VPR). The VPE and the VPR will collectively be referred to as a VPE. The VPE 405 is shown in FIG. 4 as corresponding to scan line 412-n, however each scan line has a unique virtual point of emanation with respect to the face 407 of the transducer probe 400. In this manner, the apparent emanation point is different for each scan line with respect to the face 407 of the transducer probe 400. Essentially, a unique VPE is generated for each scan line with respect to the surface of the transducer probe 400.

As mentioned above, each scan line is individually controllable in at least two dimensions, such as steering angle (theta) and elevation angle (zeta). For example, scan lines 408-1 and 408-2 differ in steering angle (theta), while scan lines 410-n and 412-n differ in elevation angle (zeta). Further, the difference in steering angle (theta) and elevation angle (zeta) between scan lines can be regular or irregular, depending on the ultrasound scan objective. Accordingly, the variation in steering angle (theta) and elevation angle (zeta) need not be uniform between the scan lines, and can indeed vary from scan line to scan line.

Figure 5:
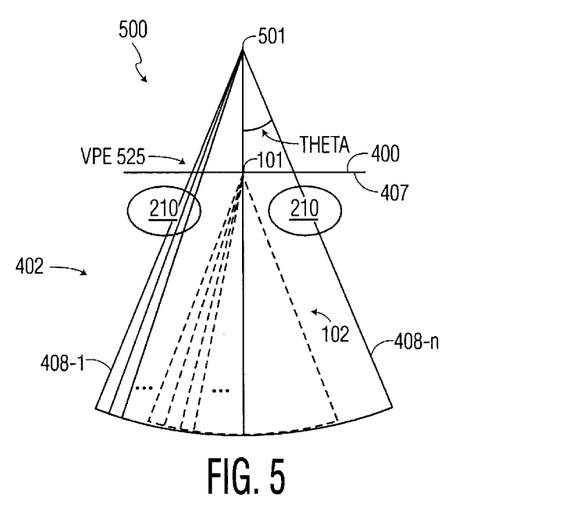
FIG. 5 is a graphical illustration showing the effect of locating the origin of the scan lines as illustrated in FIG. 4.

FIG. 5 is a graphical illustration 500 showing the effect of locating the origin of the scan lines as illustrated in FIG. 4. For comparison, the prior art scan slice 102 of FIG. 2 is illustrated in FIG. 5 using dashed lines. In accordance with an aspect of the invention, moving the origin 401 of the scan lines 408-1 through 408-n to a point other than the face 407 of the transducer probe 400, improves the ultrasound image in the near field of view. This is indicated by the portions of regions 210 that, in FIG. 5, now appear well within the scan field of view between scan lines 408-1 and 408-n. In this manner, any structures in the regions indicated using reference numeral 210 are now visible to the transducer probe 400.

As shown in FIG. 5, the virtual point of emanation (VPE) 525 of scan line 408-1 appears on the surface of the transducer probe 400 at a location other than the physical center of the transducer probe 400. The origin 501 of the scan lines 408-1 through 408-n appears behind the surface 407 of the transducer probe 400. In this manner, by varying the steering angle (theta) between each scan line 408-1 and 408-n, each scan line will have a different VPE with respect to the surface of the transducer probe 400. Further, although not shown in FIG. 5, the elevation angle (zeta) of each scan line 408-1 through 408-n can be independently varied as well, thereby allowing each scan line to appear to originate in a different location in both dimensions of the surface of the transducer probe 400.

Figure 6:
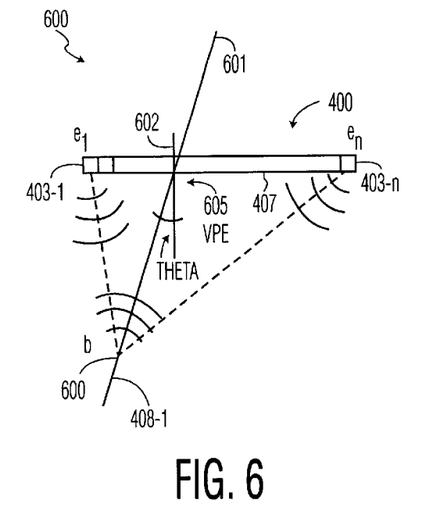
FIG. 6 is a graphical illustration showing theoretically how the transmit and receive delays are manipulated to relocate the origin of the scan lines as illustrated in FIG. 4 and FIG. 5.

FIG. 6 is a graphical illustration 600 showing theoretically how the transmit and receive delays are manipulated to relocate the origin of the scan lines as illustrated in FIG. 4 and FIG. 5. In FIG. 6, for simplicity, the transducer probe 400 is illustrated as comprising a plurality of individual transducer elements $e_1$ through $e_n$, referred to using reference numerals 403-1 through 403-n, arranged in a 1D array. However, the transmit and receive delay manipulation also applies to multidimensional transducer arrays in which the elements may be arranged in other dimensions, and in curved arrays. Further, the transducer elements may comprise what is referred to as a "mechanically wobbled" probe. A mechanically wobbled probe may include a one-dimensional array of elements that are individually mechanically translated in three-dimensional space to interrogate a three-dimensional volume. In accordance with an aspect of the invention, the origin 601 is at a point other than the surface 407 of the transducer probe 400. To move the apparent origin of the scan lines as shown, both the transmit delays and the receive delays applied to each of the transducer elements 403-1 through 403-n are altered so that appropriate focus on a target point 610 can achieve the desired apparent origin 601.

For example, during a transmit pulse, the transmit beamformer 310 delays the transmit pulse from the transducer elements 403-1 through 403-n appropriately so that the transmit energy arrives at target point 610 at the same time. This is illustrated using the scan line 408-1, which theoretically originates at the origin 601, passes through the VPE 605 on the face 407 of the transducer probe 400, and passes through the target point 610. Then, assuming that the same transducer elements are used for transmit and receive, the echoes received from the target point 610 impinge on the individual transducer elements 403-1 through 403-n and the receive beamformer 318 adjusts the delays of the transducer elements 403-1 through 403-n on receive so that the apparent receive energy appears along scan line 408-1. Since the receive delays are adjusted continuously during reception by beamformer 318, the receive focus generation is referred to as dynamic receive focus.

Said another way, the scan line control software 370 controls both the single delay profile applied by the transmit beamformer 310 and the multiple, dynamic receive delay profiles applied by beamformer 318 to the transducer elements 403-1 through 403-n so that the virtual point of emanation of each of the scan lines (i.e., scan lines 408-1 through 408-n) appears at a different location on the face 407 of the transducer probe 400. In the example shown in FIG. 6, the steering angle (theta) is at an angle other than vertical, which is depicted by the line 612, and appears at a VPE 605 other than the geographic center of the transducer probe 400.

It should be noted that the example shown in FIG. 6 assumes that each element 403-1 through 403-n on the transducer probe 400 is active. This is known as a "fully sampled aperture" transducer, as discussed previously. Apertures using fewer that all of the available transducer elements are well known and can also be used in conjunction with the scan line control software 370 (FIG. 3). For example, apertures using fewer than the total number of transducer elements 403-1 through 403-n, would result in different transmit pulses and receive echoes, but the relocation of the origin and the virtual point of emanation would still be applicable.

Figure 7:
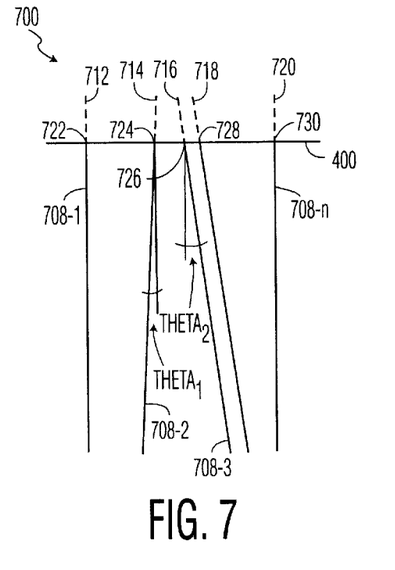
FIG. 7 is a graphical illustration showing an alternative embodiment of the invention.

FIG. 7 is a graphical illustration 700 showing an alternative embodiment of the invention. As shown in FIG. 7, a plurality of scan lines 708-1 through 708-n each have a unique point of origin. For example, the origin of scan lines 708-1 is point 712, while the origin of scan line 708-3 is point 716. Further, because the individual scan lines are all individually and uniquely controllable, each scan line can have a unique steering angle (theta) (i.e., the steering angle of scan line 708-2 is "$theta_1$" while the steering angle of scan line 708-3 is "$theta_2$"). Further, while FIG. 7 illustrates two-dimensional steering for simplicity, the concept is equally applicable to three-dimensional steering. For example, both the origins and the directions (steering in theta and zeta) of the scan lines can be distributed in three dimensions.

Figure 8:
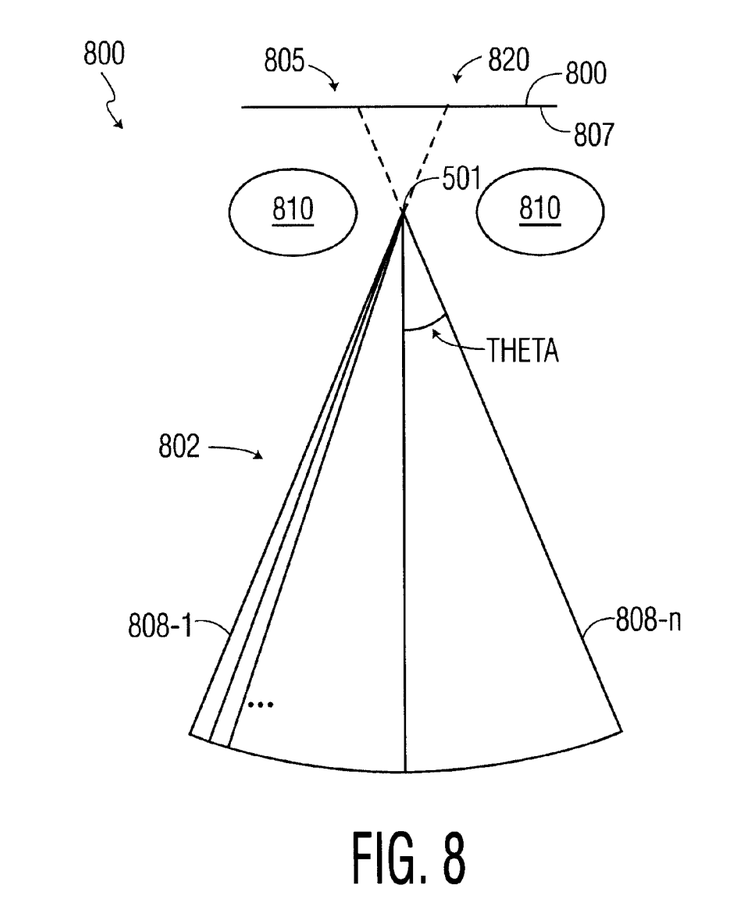
FIG. 8 is a graphical illustration showing yet another alternative embodiment of the invention.

FIG. 8 is a graphical illustration showing yet another alternative embodiment of the invention. FIG. 8 depicts scan slice 802 having an origin 801, which illustrates that the origin of the scan lines 808-1 through 808-n is moved forward with respect to the face 807 of the transducer probe 800. The origin 801 is also the virtual apex of the scan lines 808-1 through 808-n. The virtual point of emanation (VPE) of scan line 808-1 is at point 820 on the transducer probe 800, and the virtual point of emanation (VPE) of scan line 808-n is at point 805 on the transducer probe 800. In accordance with this aspect of the invention, neither the VPE 805 nor the VPE 820 are at the geographical center of the transducer probe 800, while the virtual apex is moved forward of the face 807 of the transducer probe 800. Such a scanning technique can be useful when imaging through obstructions, exemplar ones of which are illustrated using reference numeral 810.

It will be apparent to those skilled in the art that many modifications and variations may be made to the present invention, as set forth above, without departing substantially from the principles of the present invention. For example, the present invention can be used with piezoelectric ceramic and MUT transducer elements. Furthermore, the invention is applicable to various ultrasound imaging systems and components. All such modifications and variations are intended to be included herein.

What is claimed is:

1. A system for generating a three-dimensional ultrasound scan, comprising:
   a transducer probe having elements arranged in a plurality of dimensions; and
   a system controller for generating a scan line having a virtual point of emanation (VPE) in a location other than an origin projection point of said scan line.

2. The system of claim 1, wherein a plurality of scan lines comprise an ultrasound scan slice, and the system further comprises logic for instructing the system controller to generate the plurality of scan lines displaced from each other in at least two dimensions, where each scan line has a VPE at a different point on the surface of the transducer probe.

3. The system of claim 2, wherein an origin projection point associated with each of the plurality of scan lines forms a common virtual apex.

4. The system of claim 3, wherein each of the plurality of scan lines has a unique steering angle (theta).

5. The system of claim 3, wherein each of the plurality of scan lines has a unique elevation angle (zeta).

6. The system of claim 3, wherein a first of the at least two dimension corresponds to steering angle (theta) and a second of the at least two dimensions corresponds to elevation angle (zeta).

7. The system of claim 6, wherein the differences in steering angle and elevation angle among the plurality of scan lines vary by regular degrees.

8. The system of claim 3, wherein the virtual apex is located behind a face of the transducer probe.

9. The system of claim 3, wherein the virtual apex is located in front of a face of the transducer probe.

10. The system of claim 2, wherein the origin projection point of each scan line is unique and elevation angles among the plurality of scan lines vary by regular degrees.

11. The system of claim 1, wherein the transducer probe is a matrix transducer probe.

12. The system of claim 11, wherein the matrix transducer probe comprises a fully sampled array.

13. The system of claim 11, wherein the matrix transducer probe comprises a probe.

14. The system of claim 1, wherein the elements are individually translatable in three-dimensional space.

15. A method for ultrasonically interrogating a volume, comprising:
   providing a transducer probe having elements arranged in a plurality of dimensions; and
   generating a scan line having a virtual point of emanation (VPE) in a location other than an origin projection point of said scan line.

16. The method of claim 15, wherein a plurality of scan lines comprise an ultrasound scan slice, and the method further comprises generating a plurality of scan lines displaced from each other in at least two dimensions, where each scan line has a VPE at a different point on surface of the transducer probe.

17. The method of claim 16, wherein an origin projection point associated with each of the plurality of scan lines forms a common virtual apex.

18. The method of claim 17, wherein each of the plurality of scan lines has a unique steering angle (theta).

19. The method of claim 17, wherein each of the plurality of scan lines has a unique elevation angle (zeta).

20. The method of claim 17, wherein the first dimension corresponds to steering angle (theta) and the second dimension corresponds to elevation angle (zeta).

21. The method of claim 20, further comprising varying the steering angles and elevation angles among the plurality of scan lines by regular degrees.

22. The method of claim 17, further comprising generating the plurality of scan lines so that the virtual apex is located behind a face of the transducer probe.

23. The method of claim 17, further comprising generating the plurality of scan lines so that the virtual apex is located in front of a face of the transducer probe.

24. The method of claim 16, wherein the origin projection point of each scan line is unique and elevation angles among the plurality of scan lines vary by regular degrees.

25. The method of claim 16, further comprising arbitrarily positioning the at least two ultrasound scan lines with respect to one another.

26. A computer readable medium having a program for ultrasonically interrogating a volume, the program comprising logic for:

generating at least two ultrasound scan slices with a matrix transducer probe, the at least two ultrasound scan slices each including a plurality of scan lines;

where the plurality of scan lines are displaced from each other in a first dimension, and where the at least two scan slices are displaced from each other in a second dimension; and where each of the plurality of scan lines has a virtual point of emanation (VPE) at a different point on the matrix transducer probe surface.

27. A system for generating a three-dimensional ultrasound volume scan, comprising:

a two-dimensional matrix transducer probe;

a system controller for generating at least two ultrasound scan lines; and logic for instructing the system controller to generate the at least two scan lines arbitrarily displaced from each other with respect to steering angle and origin projection point.

* * * * *